(12) United States Patent
Pothukuchi et al.

(10) Patent No.: US 7,071,203 B2
(45) Date of Patent: Jul. 4, 2006

(54) PHARMACEUTICALLY ACCEPTABLE SALTS OF 20(S)-CAMPTOTHECINS

(75) Inventors: Sairam Pothukuchi, Hyderabad (IN); Subrahmanyam Duvvuri, Hyderabad (IN); Sriram Rajagopal, Hyderabad (IN)

(73) Assignees: Dr. Reddy's Laboratories Limited, Hyderabad (IN); Dr. Reddy's Laboratories, Inc., Upper Saddle River, NJ (US)

( * ) Notice: Subject to any disclaimer, the term of this patent is extended or adjusted under 35 U.S.C. 154(b) by 0 days.

(21) Appl. No.: 10/490,552

(22) PCT Filed: Sep. 25, 2002

(86) PCT No.: PCT/IB02/03950

§ 371 (c)(1),
(2), (4) Date: Mar. 23, 2004

(87) PCT Pub. No.: WO03/027118

PCT Pub. Date: Apr. 3, 2003

(65) Prior Publication Data

US 2004/0198760 A1    Oct. 7, 2004

(30) Foreign Application Priority Data

Sep. 25, 2001 (IN) .................................. 798/01

(51) Int. Cl.
*A61K 37/4745* (2006.01)
*C07D 491/22* (2006.01)

(52) U.S. Cl. ........................................ 514/283; 546/48

(58) Field of Classification Search ............... 514/283; 546/48
See application file for complete search history.

(56) References Cited

U.S. PATENT DOCUMENTS 6,177,439 B1   1/2001   Duvvuri et al.

FOREIGN PATENT DOCUMENTS

EP            1 029 863 A        8/2000

OTHER PUBLICATIONS

Database EPODOC "On Line" European Patent Office, The Hague, NL; May 16, 1990 Xueqiu Gu, et al.: "Preparation for Comptothecin Arginine Salt" XP002225687; Abstract; & CN 1 042 151 A (Xueqiu Gu).

*Primary Examiner*—Charanjit S. Aulakh
(74) *Attorney, Agent, or Firm*—Milagros A. Cepeda; Edward D. Pergament; Robert A. Franks

(57) ABSTRACT

Described are pharmaceutically acceptable salts of a compound of formula (I)

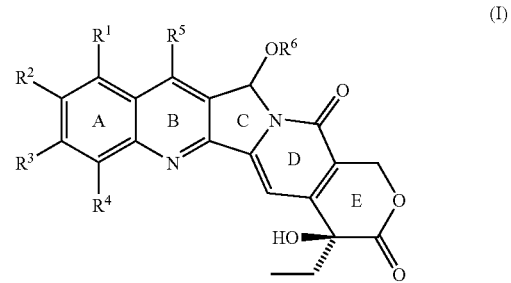

its tautomeric forms, its stereoisomers or its polymorphs, which is obtained by treating the compound of formula (I) with an acid selected from the group consisting of hydrohalo acid selected from the group consisting of hydrochloric acid or hydrobromic acid, acetic acid; sulfuric acid, nitric acid, phosphoric acid, boric acid, perchloric acid, tartaric acid, maleic acid, citric acid, methanesulfonic acid, benzoic acid, ascorbic acid, salicylic acid and benzene sulfonic acid wherein $R^1$ represents substituted ($C_1$–$C_6$) alkyl wherein the substituent(s) is selected from mono ($C_1$–$C_6$) alkylamino or di ($C_1$–$C_6$) alkylamino; $R^2$ represents hydroxy;
$R^3$, $R^4$ and $R^5$ represent hydrogen; and
$R^6$ represents hydrogen, or substituted ($C_1$–$C_6$) alkyl, wherein the substituent(s) is selected from halogen, hydroxy or ($C_1$–$C_6$) alkoxy and methods for using these compounds.

12 Claims, No Drawings

PHARMACEUTICALLY ACCEPTABLE SALTS OF 20(S)-CAMPTOTHECINS

FIELD OF THE INVENTION

The present invention relates to pharmaceutically acceptable salts formed by the compounds of general formula (I), their derivatives, their analogs, their tautomeric forms, their stereoisomers, their polymorphs and pharmaceutically acceptable compositions containing them.

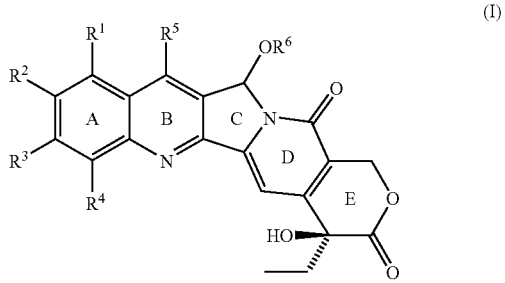

(I)

The present invention also relates to a process for the preparation of the above said pharmaceutically acceptable salts, their derivatives, their analogs, their tautomeric forms, their stereoisomers, their polymorphs, and pharmaceutical compositions containing them.

The pharmaceutically acceptable salts formed by the compounds of general formula (I) are useful for the treatment of melanoma, prostate, leukemia, lymphoma, non-small cell lung cancers, cancer of the central nervous system, breast, colon, ovarian or renal cancer.

The present invention also relates to pharmaceutical compositions containing pharmaceutically acceptable salts formed by the compounds of general formula (I) or mixtures thereof.

The pharmaceutically acceptable salts formed by the compounds of the general formula (I) have significant formulation and bulk handling advantages in view of their stability and solubility.

In our recently granted U.S. Pat. No. 6,177,439 B1, we have disclosed and described the novel compounds of the formula (II),

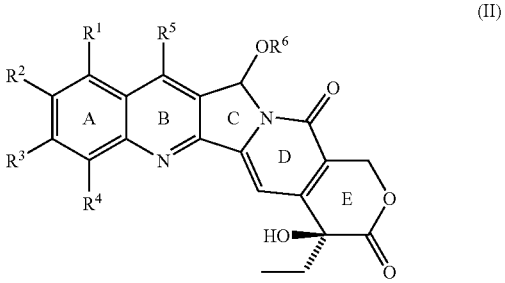

(II)

wherein $R^1$, $R^2$, $R^3$ and $R^4$ independently represent hydrogen or represent a group selected from hydroxy, lower alkoxy, lower alkanoyl, nitro, cyano, halo, carboxy, amino, substituted amino wherein the the amino group is mono or disubstituted and the substituents are selected from lower alkyl, lower haloalkyl, benzyl, benzoyl, carboxyl, amido or lower alkylamino; lower alkyl, or substituted lower alkyl wherein the substituents are selected from hydroxy, lower haloalkyl, benzyl, lower alkoxy, benzyloxy, cyano, nitro, amino or lower alkylamino; or $R^2$ and $R^3$ together represent —O—$(CH_2)_n$—O— where n=1 or 2, each of $R^1$, $R^2$, $R^3$ and $R^4$ are not the same except where each of $R^1$, $R^2$, $R^3$ and $R^4$ are hydrogen;

$R^5$ represents hydrogen, lower alkyl, substituted lower alkyl, wherein the substituents are selected from hydroxy, halogen, lower alkoxy, benzyloxy, carboxy, amido, or amino where the amino group is mono or disubstituted and the substituents are selected from lower alkyl, lower haloalkyl, benzyl, or benzoyl, when the amino group is disubstituted the substituents are independent or together with the linking nitrogen atom form a saturated 5 or 6 membered heterocyclic ring of formula (A);

(A)

where Y represents O, S, NH or $CH_2$ when formula (A) is a 5-membered ring and Y represents $CH_2$ when formula (A) is a 6-membered ring; or $R^5$ represents lower aralkyl, where the aryl group is selected from phenyl, biphenyl or naphthyl; and $R^6$ represents phenyl or benzyl where the phenyl group may be unsubstituted or substituted with mono, di or trisubstituents selected from halogen, lower alkoxy, cyano, nitro, lower alkyl, amino, or substituted amino wherein the amino group is mono or disubstituted with lower alkyl groups; cycloalkyl or cycloalkyl lower alkyl where the cyclic ring has 3 to 7 ring atoms all of the said ring atoms being carbon; lower alkyl groups substituted with saturated 5 or 6 membered heterocyclic ring of formula (B),

(B)

when formula (B) is a 5-membered ring X represents CH or N and Y represents O, S, NH or $CH_2$ when formula (B) is a 6-membered ring, X represents CH or N and Y represents $CH_2$; substituted benzoyl wherein the substituents are selected from lower alkyl, lower haloalkyl, halogen, lower alkoxy, thioalkoxy, cyano, nitro, amido, amino, or lower alkylamino; lower alkenyl; substituted lower alkyl, or substituted lower alkenyl, wherein the substituents are selected from halogen, hydroxy, lower alkoxy, aryloxy, thio, thioalkyl, thioaryl, aryl, wherein the aryl group is selected from phenyl, biphenyl, or naphthyl; heteroaryl wherein the heteroaryl is selected from pyridyl, quinoline, isoquinoline, indole, pyrrole, furan, benzofuran, thiophene, thiazolidine or imidazole; carboxy, cyano, nitro amido or amino in which the amino group can be unsubstituted or mono or disubstituted, wherein the substituents are selected from hydroxy, lower alkyl, lower haloalkyl, benzyl, benzoyl, lower alkoxy, carboxy, amido or lower alkylamino, when the amino group is disubstituted the substituents are independent or together with the linking nitrogen atom form a saturated 5 or 6 membered heterocyclic group of formula (A),

(A)

when formula (A) is a 5-membered ring, Y represents O, S, NH or CH$_2$, when formula (A) is a 6-membered ring, Y represents CH$_2$;

or R$^6$ represents substituted lower alkanoyl wherein the substituents are selected from halogen, lower alkoxy, aryloxy, thio, thioalkyl, thioaryl, aryl, wherein the aryl group is selected from phenyl, biphenyl, or naphthyl; heteroaryl wherein the heteroaryl is selected from pyridyl, quinoline, isoquinoline, indole, pyrrole, furan, benzofuran, thiophene, thiazolidine or imidazole; carboxy, cyano, nitro, amido or amino in which the amino group can be unsubstituted or mono, or disubstituted wherein the substituents are selected from hydroxy, lower alkyl, lower haloalkyl, benzyl, benzoyl, lower alkoxy, carboxy, amido, amino or lower alkylamino, when the amino group is disubstituted the substituents are independent or together with the linking nitrogen atom form a saturated 5 or 6 membered heterocyclic group of formula (A),

(A)

when formula (A) is a 5-membered ring, Y represents O, S, NH or CH$_2$; when formula (A) represents a 6-membered ring Y represents CH$_2$; and when R$^1$ represents hydroxy, amino or nitro, R$^2$, R$^3$, R$^4$ and R$^5$ represent hydrogen and R$^6$ represents hydrogen, lower alkyl, alkanoyl or benzoyl groups.

BACKGROUND OF THE INVENTION

A few closely related camptothecin derivatives, and their analogs have been reported to be useful in the treatment of cancer. Some of such compounds described in the prior art are outlined below:

(i) EP publication no. 0074256A1, U.S. Pat. Nos. 4,473,692 & 4,545,880 disclose compounds of formula (III)

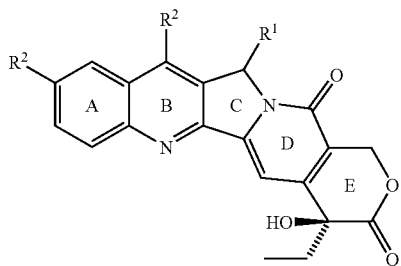

(III)

wherein R$^1$ stands for a hydrogen atom, an alkyl group, a hydroxyl group, an alkoxy group or an acyloxy group; R$^2$ for a hydrogen atom, an alkyl group, an aralkyl group, a hydroxymethyl group, a carboxymethyl group or an acyloxymethyl group, and R$^3$ for the grouping —XR' (where R' is a hydrogen atom, an alkyl group or an acyl group and X is an oxygen atom or a sulfur atom), a nitro group, an amino group, an alkylamino group, an acylamino group or a halogen atom, with the proviso that when both of R$^1$ and R$^2$ are hydrogen atoms, R$^3$ should not be hydroxyl group, methoxy group or acetoxy group.

An example of these compounds is shown in formula (IIIa)

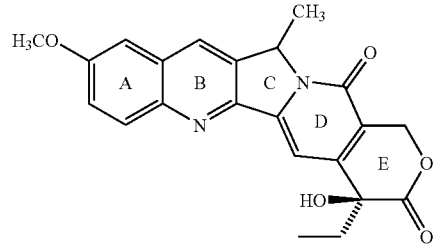

(IIIb)

(ii) GB patent no. 2056973 discloses compounds of formula (IV)

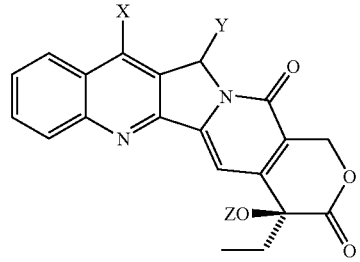

(IV)

wherein X is H, CH$_2$OH, COOH, an alkyl group, an aralkyl group or the grouping CH$_2$OR$^1$ or CH$_2$OR$^2$ wherein R$^1$ is an alkyl group or an acyl group and R$^2$ is a lower alkyl group, Y is H, OH or the grouping OR$^3$ wherein R$^3$ is a lower alkyl group or an acyl group, and Z is H or an acyl group, with certain combinations excluded, and water soluble alkali metal salts thereof, are prepared by introduction of a substituent at X or Y optionally followed by modification of those and/or other substituents.

An example of these compounds is shown in formula (IVa)

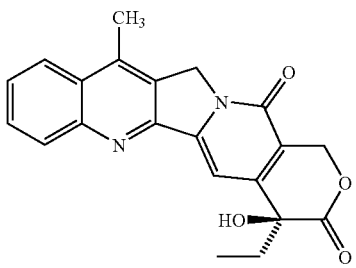

(IVa)

(iii) The European Publication no. EP 321122 discloses topotecan of formula (III), which is already marketed

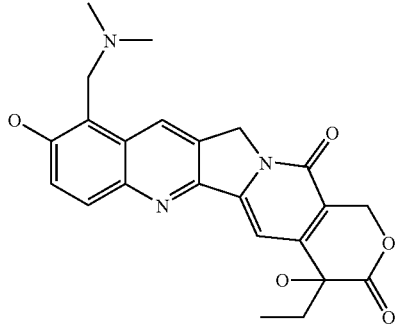

(V)

OBJECTIVE OF THE INVENTION

The main objective of the present invention is therefore to provide pharmaceutically acceptable salts formed by the 20(S)-camptothecin dervatives of the general formula (I), their analogs, their tautomeric forms, their stereoisomers, their polymorphs and pharmaceutical compositions containing them or their mixtures having good stability and solubility, which can be used for the treatment of melanoma, prostate, leukemia, lymphoma, non-small lung cancers, cancer of the central nervous system, breast, colon, ovarian, renal cancers or other cancers which are resistant to drugs like Adriomycin, Topotecan, Irinotecan, Cisplatinate and the like, with better efficacy, potency and lower toxicity.

Yet another objective of the present invention is to provide a process for the preparation of pharmaceutically acceptable salts formed by the 20(S)-camptothecin derivatives of the general formula (I) as defined above, their analogs, their tautomeric forms, their stereoisomers and their polymorphs Still yet another objective of the present invention is to provide pharmaceutical compositions containing pharmaceutically acceptable salts formed by the compounds of the general formula (I), their analogs, their derivatives, their tautomers, their stereoisomers, their polymorphs or their mixtures in combination with suitable carriers, solvents, diluents and other media normally employed in preparing such compositions.

DETAILED DESCRIPTION OF THE INVENTION

The present invention relates to pharmaceutically acceptable salts formed by the compounds of the general formula (I)

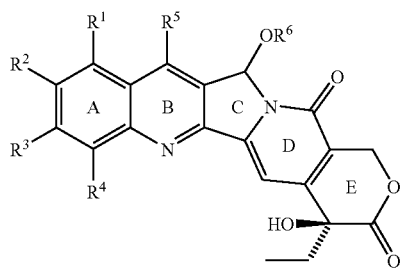

(I)

their derivatives, their analogs, their tautomeric forms, their stereoisomers, their polymorphs and pharmaceutically acceptable compositions, wherein $R^1$ represents substituted $(C_1-C_6)$alkyl wherein the substituents are selected from mono$(C_1-C_6)$alkylamino or di$(C_1-C_6)$alkylamino; $R^2$ represents hydroxy; $R^3$, $R^4$ and $R^5$ represent hydrogen;

and $R^6$ represents hydrogen, substituted $(C_1-C_6)$alkyl, wherein the substituents are selected from halogen, hydroxy or $(C_1-C_6)$alkoxy group.

Suitable groups represented by $R^1$ are selected from substituted $(C_1-C_6)$alkyl such as substituted methyl, substituted ethyl, substituted n-propyl, substituted isopropyl and the like; wherein the substituents are selected from $(C_1-C_6)$alkylamino such as methylamino, ethylamino, n-propylamino, iso-propylamino and the like or di$(C_1-C_6)$alkylamino such as dimethylamino, diethylamino, dipropylamino and the like.

Suitable groups represented by $R^6$ are selected from hydrogen or substituted $(C_1-C_6)$alkyl such as substituted methyl, substituted ethyl, substituted n-propyl, substituted iso-propyl and the like; wherein the substituents are selected from halogen atom such as fluorine, chlorine, bromine, iodine; hydroxy group or $(C_1-C_6)$alkoxy such as methoxy, ethoxy, propoxy and the like.

Particularly useful compounds according to the present invention include:
10-Hydroxy-9-N,N-dimethylaminomethyl-5-hydroxy-[20(S),5(R)]-camptothecin hydrochloride;
10-Hydroxy-9-N,N-dimethylaminomethyl-5-hydroxy-[20(S),5(S)]-camptothecin hydrochloride;
10-Hydroxy-9-N,N-dimethylaminomethyl-5-hydroxy-[20(S),5(RS)]-camptothecin hydrochloride;
10-Hydroxy-9-N,N-dimethylaminomethyl-5-(2'-hydroxyethoxy)-[20(S),5(R)]-camptothecin hydrochloride;
10-Hydroxy-9-N,N-dimethylaminomethyl-5-(2'-hydroxyethoxy)-[20(S),5(S)]-camptothecin hydrochloride;
10-Hydroxy-9-N,N-dimethylaminomethyl-5-(2'-hydroxyethoxy)-[20(S),5(RS)]-camptothecin hydrochloride;
10-Hydroxy-9-N,N-dimethylaminomethyl-5-(2'-methoxyethoxy)-[20(S),5(R)]-camptothecin hydrochloride;
10-Hydroxy-9-N,N-dimethylaminomethyl-5-(2'-methoxyethoxy)-[20(S),5(S)]-camptothecin hydrochloride;
10-Hydroxy-9-N,N-dimethylaminomethyl-5-(2'-methoxyethoxy)-[20(S),5(RS)]-camptothecin hydrochloride;
10-Hydroxy-9-N,N-dimethylaminomethyl-5-(2'-fluoroethoxy)-[20(S),5(R)]-camptothecin hydrochloride;
10-Hydroxy-9-N,N-dimethylaminomethyl-5-(2'-fluoroethoxy)-[20(S),5(S)]-camptothecin hydrochloride and
10-Hydroxy-9-N,N-dimethylaminomethyl-5-(2'-fluoroethoxy)-[20(S),5(RS)]-camptothecin hydrochloride.

According to the present invention, there is provided a process for the preparation of pharmaceutically acceptable salts formed by the compounds of the general formula (I) which comprises: reacting compound of the formula (II)

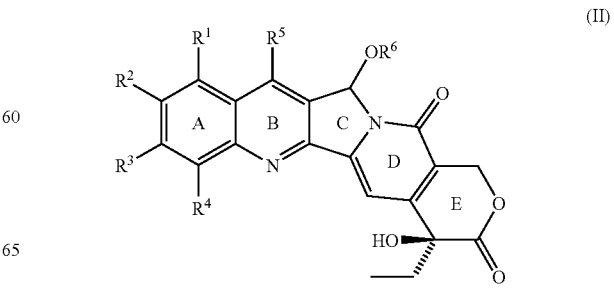

(II)

where all symbols are as defined earlier with a stoichiometric amount of an appropriate acid in the presence of a solvent at a temperature in the range of 20 to 100° C. for a period in the range 2–9h.

The compound of the formula (II) used may be either in optically pure form or in racemic form and are prepared by a procedure reported in U.S. Pat. No. 6,177,439 B1.

The pharmaceutically acceptable salts are prepared by reacting the compound of formula (I) with hydrohalo acid selected from hydrochloric acid or hydrobromic acid, acetic acid, sulfuric acid, nitric acid, phosphoric acid, boric acid, perchloric acid, tartaric acid, maleic acid, citric acid, methanesulfonic acid, benzoic acid, ascorbic acid, salicylic acid, benzene sulfonic acid and the like. The solvent employed may be selected from ketones such as acetone, diethyl ketone, methyl ethyl ketone or their mixtures, methanol, ethanol, n-hexane, ethylacetate, benzene, diethylamine, formaldehyde, chloroform, dichloromethane or mixture thereof.

Various polymorphs of a pharmaceutically acceptable salts formed by the compounds of the general formula (I), forming part of this invention may be prepared by crystallization of pharmaceutically acceptable salts formed by the compounds of the general formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry (DSC), powder X-ray diffraction or such other techniques.

The stereoisomers of the compounds forming part of this invention may be prepared by using pharmaceutically acceptable salts formed by the compounds of the general formula (I) in its single diastereoisomeric form in the process by resolving the mixture of stereoisomers by conventional methods. Commonly used methods are compiled by Jaques et. al in "Enantiomers, Racemates and Resolution" (Wiley Interscience, 1981).

The present invention provides a pharmaceutical composition, containing the salts formed by the pharmaceutically acceptable salts formed by the compounds of the general formula(I) as defined above, their derivatives, their analogs, their tautomeric forms, their stereoisomers, their polymorphs, their pharmaceutically acceptable solvates in combination with the usual pharmaceutically employed carriers, diluents and the like, useful for the treatment of leukemia, lymphoma, non-small cell lung cancer, cancer of the central nervous system, breast, colon, ovarian, renal cancer or other cancers which are resistant to drugs like Adriomycin, Topotecan, Irinotecan, Cisplatinate and the like.

The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. Such compositions typically contain from 1 to 20%, preferably 1 to 10% by weight of active compound, the remainder of the composition being pharmaceutically acceptable carriers, diluents or solvents.

Suitable pharmaceutically acceptable carriers include solid fillers or diluents and sterile aqueous or organic solutions. The active ingredient will be present in such pharmaceutical compositions in the amounts sufficient to provide the desired dosage in the range as described above. Thus, for oral administration, the active ingredient can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the active ingredient can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or salts with base of the compounds. Aqueous solutions with the active ingredient dissolved in polyhydroxylated castor oil may also be used for injectable solutions. The injectable solutions prepared in this manner can then be administered intravenously, intraperitoneally, subcutaneously, or intramuscularly, with intramuscular administration being preferred in humans.

For nasal administration, the preparation may contain the active ingredient of the present invention dissolved or suspended in a liquid carrier, in particular an aqueous carrier, for aerosol application. The carrier may contain additives such as solubilizing agents, such as propylene glycol, surfactants, absorption enhancers such as lecithin (phosphatidylcholine) or cyclodextrin or preservatives such as parabenes.

Tablets, dragees or capsules having talc and/or a carbohydrate carried binder and the like are particularly suitable for any oral application. Preferably, carriers for tablets, dragees or capsules include lactose, cornstarch and/or potato starch. A syrup or elixir can be used in cases where a sweetened vehicle can be employed.

The pharmaceutically acceptable salts formed by the compounds of the general formula (I) as defined above are clinically administered to mammals, including man, via either oral, nasal, pulmonary, transdermal or parenteral, rectal, depot, subcutaneous, intravenous, intraurethral, intramuscular, intranasal, ophthalmic solution or an ointment. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.01 to about 100 mg/kg body weight of the subject per day or preferably about 0.01 to about 30 mg/kg body weight per day administered singly or as a divided dose. However, the optimum dosage for the individual subject being treated will be determined by the person responsible for treatment, generally smaller doses being administered initially and thereafter increments made to determine the most suitable dosage.

The compounds of the present invention are successfully implemented in the treatment of melanoma, prostate, leukemia, lymphoma, non-small cell lung cancers, cancer of the central nervous system, breast, colon, ovarian, renal cancer or other cancers which are resistant to drugs like Adriomycin, Topotecan, Irinotecan, Cisplatinate and the like. This was demonstrated by in vitro as well as in vivo animal experiments.

The invention is explained in detail in the examples given below which are provided by way of illustration only and therefore should not be construed to limit the scope of the invention.

Preparation 1

10-Hydroxy-9-N,N-dimethylaminomethyl-5-hydroxy-20(S)-camptothecin

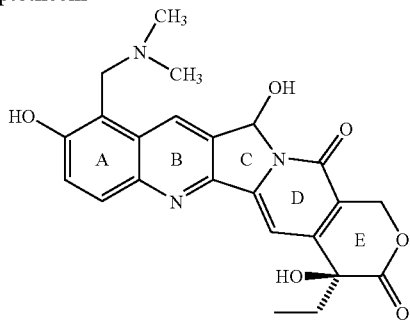

To a mixture of 10-hydroxy-9-N,N-dimethylaminoethyl-20(S)-camptothecin (200 mg) [prepared according to the procedure as described by (1) J. L. Wood et. al, in *J. Org. Chem.*, 5739–5740 (1995); (2) A. Pochini et. al, in *Synthesis*, 906 (1983)] and ferric chloride (200 mg), dissolved in ethanol (20 ml), sulfuric acid (2 ml) was added dropwise and heated at 80° C. for 20 h. Excess acid and ethanol were removed under vacuum and the residue was neutralized with potassium carbonate solution and extracted with ethyl acetate. The organic layer was washed with water, brine and dried over anhydrous sodium sulfate. Evaporation of the solvent afforded a solid material. Purification of the solid residue over silica gel column chromatography using methanol-chloroform as an eluent yielded 10-hydroxy-9-N,N-dimethylamino methyl-5-ethoxy-20(S)-camptothecin (160 mg) as yellowish powder.

10-Hydroxy-9-N,N-dimethylaminomethyl-5-ethoxy-20(S)-camptothecin (160 mg) was dissolved in ethanol (10 ml) and treated with 50% HCl (10 ml). The solution was heated to reflux for 20 h. At the end of the reaction, excess water and ethanol were removed as an azeotropic mixture and the residue was neutralized with potassium carbonate solution and extracted with ethyl acetate. The organic layer was washed with brine and dried over anhydrous sodium sulfate. Concentration of the solvent afforded 10-hydroxy-9-N,N-dimethylaminomethyl-5-hydroxy-20(S)-camptothecin (100 mg) after purification over silica gel column chromatography using ethyl acetate-chloroform as an eluent, mp: 245° C.

$^1$H-NMR (DMSO): δ 11.7 (s, D$_2$O exchangeable, 1H), 10.0 (s, D$_2$O exchangeable, 1H), 8.95 (s, 1H), 8.10 (d, J=10.0 Hz, 1H), 7.70 (d, J=10.0 Hz, 1H), 7.20 (s, 1H), 6.95 (s, 0.5H), 6.85 (s, 1H), 5.40 (s, 2H), 4.70 (s, 2H), 4.70 (s, 2H), 2.40 (s, 6H), 1.95–1.80 (m, 2H), 0.95–0.75 (m, 3H).

Preparation 2

10-Hydroxy-9-N,N-dimethylaminomethyl-5-(2'-hydroxyethoxy)-20(S)-camptothecin

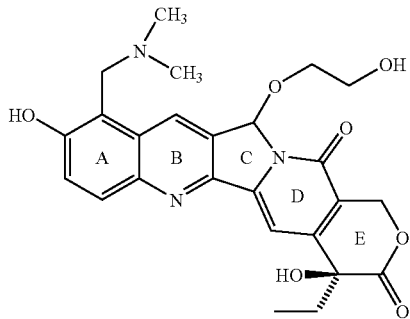

To a mixture of 10-hydroxy-9-N,N-dimethylaminoethyl-20(S)-camptothecin (50 mg) [prepared according to the procedure as described by (1) J. L. Wood et. al, in *J. Org. Chem.*, 5739–5740 (1995); (2) A. Pochini et. al, in *Synthesis*, 906 (1983)] and ferric chloride (50 mg), dissolved in ethyleneglycol (8 ml), sulfuric acid (0.6 ml) was added dropwise and heated at 90° C. for 10 h. Excess acid and ethyleneglycol were removed under vacuum and the residue was neutralized with potassium carbonate solution and extracted with 5% methanol-ethyl acetate. The organic layer was washed with water, brine and dried over anhydrous sodium sulfate. Concentration of the solvent afforded a solid material. Purification of the solid residue over silica gel column chromatography using methanol-chloroform as an eluent yielded 10-hydroxy-9-N,N-dimethylamino_methyl-5-(2'-hydroxyethoxy)-20(S)-camptothecin (25 mg) as yellowish powder, mp: 220° C.

$^1$H-NMR (DMSO): δ 11.7 (s, D$_2$O exchangeable, 1H), 9.90 (s, D$_2$O exchangeable, 1H), 8.85 (s, 1H), 8.20 (d, J=10.0 Hz, 1H), 7.70 (d, J=10.0 Hz, 1H), 7.20 (s, 1H), 6.95 (s, 0.5H), 6.85 (s, 0.5H), 5.40 (s, 2H), 4.75 (s, 2H) 3.90–3.70 (m, 4H), 2.80 (s, 6H), 1.95–1.75 (m, 2H), 0.95–0.75 (m, 3H).

Preparation 3

10-Hydroxy-9-N,N-dimethylaminomethyl-5-(2'-fluoroethoxy)-20(S)-campto thecin

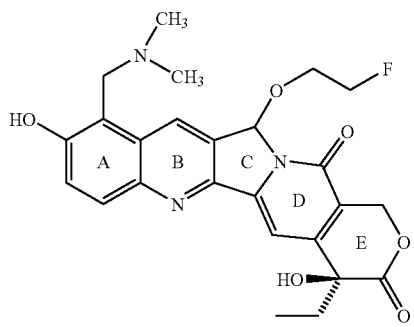

To a mixture of 10-hydroxy-9-N,N-dimethylaminomethyl-5-hydroxy-20(S)-camptothecin (50 mg) (obtained in preparation 1) and sulfuric acid (0.1 ml) suspended in dichloromethane (10 ml), 2-fluoroethanol (0.2 ml) was added and heated the mixture to reflux temperature for 12 h. The reaction was quenched with water and extracted with ethyl acetate. The organic layer was washed with water, brine and concentrated to dryness. The residue was purified by silica gel column chromatography using acetone-chloroform as an eluent to yield 10-hydroxy-9-N,N-dimethylaminomethyl-5-(2-fluoroethoxy)-20(S)-camptothecin (25 mg). mp: 200° C.

$^1$H-NMR (DMSO): δ 8.97 (s, 1H), 8.18 (d, J=9.4 Hz, 1H), 7.78 (d, J=9.4 Hz, 1H), 7.19–7.17 (s, 1H), 6.94 (s, 1H), 6.88 (s, 1H), 5.40 (br, s, 2H), 4.80 (br, s, 2H), 4.70 (m, 2H), 4.20 (m, 2H), 2.80 (br, s, 3H), 1.87 (br, m, 2H), 0.88 (br, m, 3H).

EXAMPLE 1

10-Hydroxy-9-N,N-dimethylaminomethyl-5-hydroxy-20(S)-camptothecin hydrochloride

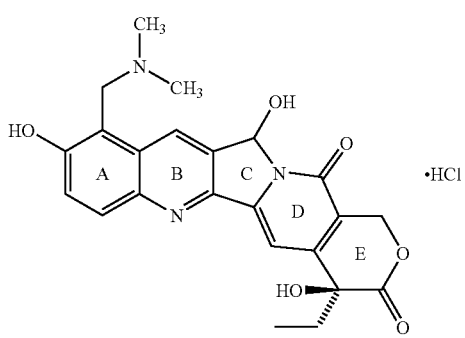

A Mixture of 10-hydroxy-9-N,N-dimethylaminomethyl-5-hydroxy-20(S)-camptothecin (50 mg) (obtained in preparation 1), 0.4 N aqueous HCl (5 ml) was heated while stirring for 4 h. Then ethylacetate (40 ml) was poured into the reaction mixture in 3 lots. Refluxed for ~10 min each time. Decanted the organic layers. Washed with 10% acetone: chloroform. Finally aqueous layer was evaporated as benzene azeotrope at ~80° C. on rotavapour. The solid obtained was washed with ethylacetate and dried.

$^1$H-NMR (DMSO, 200 MHz): δ 11.78 (s, 1H), 10.0 (bs, 1H), 8.9 (s, 1H), 8.1 (dd, 2H), 7.18 (d, 1H), 6.9 (d, 1H), 5.4 (s, 2H), 4.7 (s, 2H), 2.8 (d, 6H), 1.8 (bs, 2H), 0.9 (bs, 3H).

EXAMPLE 2

10-Hydroxy-9-N,N-dimethylaminomethyl-5-(2'-hydroxyethoxy)-20(S)-camptothecin hydrochloride

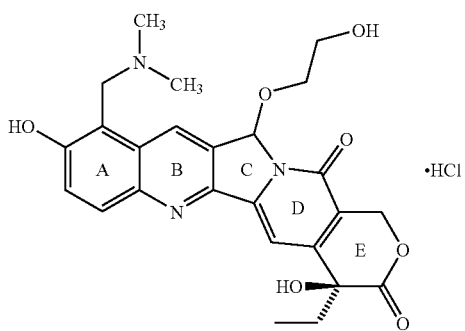

A Mixture of 10-hydroxy-9-N,N-dimethylaminomethyl-5-(2'-hydroxyethoxy)-20(S)-camptothecin (60 mg) (obtained in preparation 2) and 0.4 N aqueous HCl (6 ml) was heated while stirring for 4 h. Then ethylacetate (50 ml) was poured into the reaction mixture in 3 lots. Refluxed for ~10 min each time. Decanted the organic layers. Washed with 10% acetone: chloroform. Finally water was evaporated as benzene azeotrope at 80° C. on rotavapour. The solid obtained was washed with ethylacetate and dried.

$^1$H-NMR (DMSO, 200 MHz): δ 8.63 (s, 1H), 7.95 (d, 1H), 7.4 (m, 2H), 6.9 (d, 1H), 5.4 (dd, 2H), 4.3–3.3 (bs, 8H), 2.5 (s, 6H), 1.9 (q, 2H), 0.9 (t, 3H).

EXAMPLE 3

10-Hydroxy-9-N,N-dimethylaminomethyl-5-(2'-fluoroethoxy)-20(S)-camptothecin hydrochloride

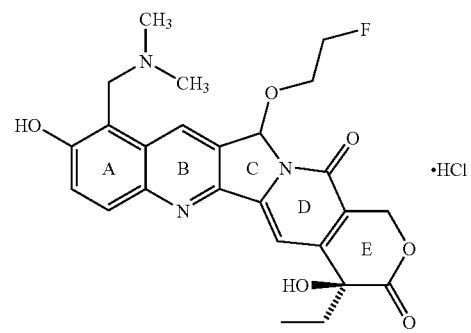

Dissolved 10-hydroxy-9-N,N-dimethylaminomethyl-5-(2'-fluoroethoxy)-20(S)-camptothecin (5 g) in 0. 1N hydrochloric acid (120 ml) and filtered to remove undissolved matter. The filtrate was washed successively with ethyl acetate (25 ml×4) and the aqueous solution was lyophilized. After lyophilization, dried the resultant product in vacuum for 16 h at room temperature and was crystallized from ethanol (50 ml) and hexane (100 ml). The product was filtered and dried in vacuum for 24 h at room temperature. Yield: 4.5 g.

$^1$H-NMR (DMSO, 200 MHz): δ 8.97 (s, 1H), 8.18 (d, J=9.4 Hz, 114), 7.78 (d, J=9.4 Hz, 1H), 7.19–7.17 (s, 1H), 6.94 (s, 1H), 6.88 (s, 1H), 5.40 (br, s, 2H), 4.80 (br, s, 2H), 4.70 (m, 2H), 4.20 (m, 2H), 2.80 (br, s, 3H), 1.87 (br, m, 2H), 0.88 (br, m, 3H).

Anti-Cancer Activity:

The compounds prepared in the present invention exhibited very good in vitro anti-cancer activity towards various human tumor cell lines.

Each test compound was screened against a battery of cell lines representing eight different types of cancers. In a typical procedure, 1×10$^4$ cells were seeded into each well of 96 well plate in 100 μL volume of RPMI 1640 medium containing antibiotics and 10% FCS.

The plates were incubated at 37° C. in presence of CO$_2$. After 24 h, test compounds were evaluated at five 10-fold dilutions ranging from 100 to 0.01 μM. To each test well 100 μL of test compound solution was added and medium with vehicle was added to control wells and the plates were further incubated. After 48 h of incubation, plates were terminated by Sulforhodamine B method.

The optical density, which is proportional to protein mass, is then read by automated spectrophotometric plate reader at a wavelength of 515 nm. Readings were transferred to a microcomputer and mean 50% Growth Inhibition (GI50) and mean Total Growth Inhibition were calculated. The compounds of the present invention showed anticancer activity, which can be seen from the data given below:

TABLE 1

Growth Inhibition (GI 50) and Total Growth Inhibition (TGI) values for different cell lines (EXAMPLE 1)

| PANEL | CELL LINES | | | | | | |
|---|---|---|---|---|---|---|---|
| | CNS: SF-268 | OVARIAN: OVCAR-8 | BREAST: MCF-7/ADR | PROSTATE: DU-145 | RENAL: ACHN | LUNG: HOP-62 | MELANOMA: UACC-62 |
| GI 50 [µM] | 0.55 | 0.5 | 0.25 | 0.4 | 0.4 | 0.6 | 0.7 |
| TGI [µM] | 90.0 | >100 | 0.9 | 0.8 | 1.0 | 25.0 | 4.5 |

TABLE 2

Growth Inhibition (GI 50) and Total Growth Inhibition (TGI) values for different cell lines (EXAMPLE 2)

| PANEL | CELL LINES | | | | | | |
|---|---|---|---|---|---|---|---|
| | CNS: SF-268 | OVARIAN: OVCAR-8 | BREAST: MCF-7/ADR | PROSTATE: DU-145 | RENAL: ACHN | LUNG: HOP-62 | MELANOMA: UACC-62 |
| GI 50 [µM] | 7.5 | 1.0 | 7.5 | 5.5 | 4.0 | 8.0 | 6.0 |
| TGI [µM] | >100 | 80.0 | 50.0 | 25.0 | 40.0 | >100 | 6.0 |

TABLE 3

Growth Inhibition (GI 50) and Total Growth Inhibition (TGI) values for different cell lines (EXAMPLE 3)

| PANEL | CELL LINES | | | | | | | | | | |
|---|---|---|---|---|---|---|---|---|---|---|---|
| | CNS: U251 | OVARIAN: | | BREAST: | | PROSTATE: | | RENAL: A 498 | LUNG: H 522 | MELANOMA: UACC-62 | COLON: SW-620 |
| | | SKOV-3 | PA-1 | MCF 7/ADR | MCF 7 | DU-145 | PC-3 | | | | |
| GI 50 [µM] | 1.5 | 6.0 | 1.0 | 8.0 | 7.5 | 4.0 | 9.0 | 0.7 | 0.9 | 1.5 | 60.0 |
| TGI [µM] | >100 | 40.0 | 5.0 | >100 | 10.0 | >100 | >100 | 15.0 | 90.0 | 8.0 | >100 |

Solubility by RPLC Method:

Excess of compound was soaked in 0.5 ml of 0.1 M sodium acetate buffer at pH 5.0 for 24 h at room temperature. The solution was filtered through 0.45 micron PVDF syringe filter (Gelman Sciences). The filtrate was injected into HPLC at different volumes (10 & 20 µl). Chromatograms were recorded. Responses recorded were extrapolated from the calibration curve and the solubility of the compound was calculated. (J. Med. Chem., 1995, 38, 400).

TABLE 4

Solubility by HPLC method

| Solubility | Example 3 |
|---|---|
| By HPLC method | 300 mg/ml |

Single Dose Oral Pharmacokinetic Studies:

Animals:

Male Swiss Albino Mice (20–30 g) were used in the experiments. The animals were maintained under standard laboratory conditions and had free access to feed and water ad libitum. Before experimentation animals were fasted overnight (~15 h) during which they had free access to water ad libitum.

Dose Preparation and Administration:

An amount equivalent to 10 mg of drug was weighed accurately and transferred into a clean mortar and triturated to obtain a fine powder. To this 500 µl of DMSO (10%) was added to obtain a clear solution. To this 4.5 ml of sodium carboxy methyl cellulose (sodium CMC) was added to make up the volume to 5 ml. Based on the animal weight appropriate volume (body weight in grams×10=no. of µl of dose to be given) of the prepared solution was administered through oral gavage.

Animal Experimentation:

After dosing, at designated time points (0.5, 1, 2, 3, 5, 8 and 12 h) 100 µl of blood was collected from retro orbital plexus into 0.5 ml eppendorff tubes containing EDTA (5 µl of 200 mg/ml solution in Milli Q water). Blood was centrifuged at 12,800 rpm for 2 min and plasma was separated and immediately taken for analysis, without delay, in order to estimate both lactone and carboxylate forms of the compound.

Bio-Analysis Procedure:

50 µl plasma was transferred into a clean 2 ml micro centrifuge tube. To this ice cold methanol was added (450 µl) and vertex mixed for 15 sec to extract the compound. These contents were centrifuged for 2 min at 12,800 rpm dry centrifuge tube. Clear supernatant was separated in to a 300 µl of auto sampler vial maintained at 4° C. and 20 µl of this was injected into HPLC column.

HPLC Conditions:

HPLC system (Shimadzu) consisted of system controller (SCL-10AVP), Isocratic pump (LC-10ATVP), auto sampler (SIL-10ADVP), fluorescence detector (RF-10AXL) and column oven at 25° C. (CTO-1OASVP) was controlled by Class-VP software. Sample was eluted through column (Supelcosil-LC318, 5μ, 4.6×250 mm, 300° A) with mobile phase [1% TEAA (pH=5.5):Acetonitrile:MeOH::80:15:5] pumped at 1.0 ml/min flow rate and eluent was detected using fluorescence detector set at Ex. 370 nm/Em. 537 nm. The approx. RTs were carboxylate (CA1=4.1 min, CA2=4.8 min) and lactone (LA1=7.9 min, LA2=11.6 min).

Calibration and Determination of Concentration:

For the determination of drug concentration, peak area ratios of the drug to internal standard versus the concentration (range: 0.05–10 μg/ml) for both carboxylate and lactone forms were plotted separately and linear regression was applied using software "Sigma Plot" (Jandel Scientific version, 2.0, USA). Correlation coefficients ($r^2$) of 0.99 or better were obtained.

Computation and Data Analysis:

Pharmacokinetic parameters were calculated for both carboxylate and lactone forms separately by non-compartmental model analysis. The peak plasma concentration ($C_{max}$) and the corresponding time ($T_{max}$) were directly obtained from the raw data. The area under the plasma concentration versus time curve up to the last quantifiable time point, $AUC_{(0-t)}$ was obtained by the linear and log-linear trapezoidal summation. The $AUC_{(0-t)}$ extrapolated to infinity (i.e., $AUC_{(0-\infty)}$) by adding the quotient of $C_{last}/K_{el}$, where $C_{last}$ represents the last measurable time concentration and $K_{el}$ represents the apparent terminal rate constant. $K_{el}$ was calculated by the linear regression of the log-transformed concentrations of the drug in the terminal phase. The half-life of the terminal elimination phase was obtained using the relationship $t_{1/2}=0.693/K_{el}$.

TABLE 4

Pharmacokinetic parameters (EXAMPLE 3)

| Parameter | | Oral (n = 3) | |
|---|---|---|---|
| | | Lactone | Oral |
| $AUC_{(0-t)}$ | μM · hr | 6.10 | 11.05 |
| $AUC_{(0-\infty)}$ | μM · hr | 9.74 | 15.14 |
| $C_{max}$* | μM | 3.36 | 5.88 |
| $T_{max}$ | hr | 0.25 | 0.25 |
| $K_{el}$ | $hr^{-1}$ | 0.19 | 0.20 |
| $T_{1/2\beta(4,6,8h)}$@ | hr | 7.04 | 4.38 |

We claim:

1. A compound of the formula (I)

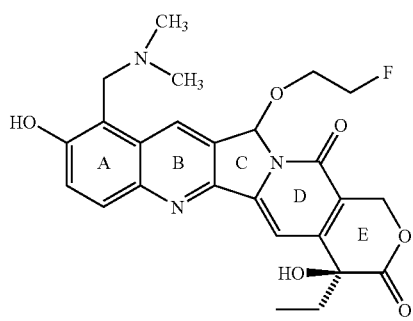

its tautomeric forms, its stereoisomer thereof, and their pharmaceutically acceptable salts.

2. A pharmaceutical composition, which comprises an effective amount of a pharmaceutically acceptable salt according to claim 1, and a pharmaceutically acceptable carrier, diluent, excipient or solvate.

3. A pharmaceutical composition as claimed in claim 2, in the form of a tablet, capsule, powder, syrup, solution or suspension.

4. A method of treating melanoma, prostate cancer, leukemia, lymphoma, non-small cell lung cancers, cancer of the central nervous system, breast, colon, ovarian or renal cancer, which comprises administering an effective amount of a pharmaceutically acceptable salt as claimed in claim 1, to a patient in need thereof.

5. A pharmaceutically acceptable salt of a compound of the formula (I), a tautomeric form, or a stereoisomer thereof in accordance with claim 1, wherein the pharmaceutical salt is a hydrochloride.

6. A pharmaceutical composition, which comprises an effective amount of a pharmaceutically acceptable salt according to claim 5, and a pharmaceutically acceptable carrier, diluent, excipient or solvate.

7. A pharmaceutical composition as claimed in claim 6, in the form of a tablet, capsule, powder, syrup, solution or suspension.

8. A method of treating melanoma, prostate cancer, leukemia, lymphoma, non-small cell lung cancers, cancer of the central nervous system, breast, colon, ovarian or renal cancer, which comprises administering an effective amount of a pharmaceutically acceptable salt as claimed in claim 5, to a patient in need thereof.

9. A salt according to claim 1, selected from:

10-Hydroxy-9-N,N-dimethylaminomethyl-5-(2-fluoroethoxy)-[20(S),5(R)]camptothecin hydrochloride;

10-Hydroxy-9-N,N-dimethylaminomethyl-5-(2'-fluoroethoxy)-[20(S),5(S)]camptothecin hydrochloride and 10-Hydroxy-9-N,N-dimethylaminomethyl-5-(2'-fluoroethoxy)-[20(S),5(RS)]camptothecin hydrochloride.

10. A pharmaceutical composition, which comprises an effective amount of a pharmaceutically acceptable salt according to claim 9, and a pharmaceutically acceptable carrier, diluent, excipient or solvate.

11. A pharmaceutical composition as claimed in claim 10, in the form of a tablet, capsule, powder, syrup, solution or suspension.

12. A method of treating melanoma, prostate cancer, leukemia, lymphoma, non-small cell lung cancers, cancer of the central nervous system, breast, colon, ovarian or renal cancer, which comprises administering an effective amount of a pharmaceutically acceptable salt as claimed in claim 9 to a patient in need thereof.

* * * * *